(12) United States Patent
Jaeger (10) Patent No.: US 9,267,837 B2
(45) Date of Patent: Feb. 23, 2016

(54) METHODS AND SYSTEMS FOR ACTIVE LOAD WEIGHT FOR MINING EXCAVATING EQUIPMENT

(71) Applicant: Siemens Industry, Inc., Alpharetta, GA (US)

(72) Inventor: Julian D. Jaeger, Atlanta, GA (US)

(73) Assignee: SIEMENS INDUSTRY, INC., Alpharetta, GA (US)

( * ) Notice: Subject to any disclaimer, the term of this patent is extended or adjusted under 35 U.S.C. 154(b) by 0 days.

(21) Appl. No.: 14/230,041

(22) Filed: Mar. 31, 2014

(65) Prior Publication Data

US 2015/0276468 A1 Oct. 1, 2015

(51) Int. Cl.

| | | |
|---|---|---|
| G06K 9/00 | (2006.01) |
| E21C 37/00 | (2006.01) |
| E02F 1/00 | (2006.01) |
| G01G 9/00 | (2006.01) |
| G06T 7/00 | (2006.01) |
| G06T 7/60 | (2006.01) |
| G01G 19/00 | (2006.01) |
| G01N 9/00 | (2006.01) |
| E02F 9/26 | (2006.01) |
| G01G 19/08 | (2006.01) |

(52) U.S. Cl.
CPC *G01G 9/00* (2013.01); *E02F 9/261* (2013.01); *E02F 9/264* (2013.01); *G01G 19/00* (2013.01); *G01G 19/08* (2013.01); *G01N 9/00* (2013.01); *G06T 7/0075* (2013.01); *G06T 7/602* (2013.01); *G06T 2207/10012* (2013.01); *G06T 2207/30181* (2013.01)

(58) Field of Classification Search
CPC ........ G01G 9/00; G01G 19/00; G06T 7/0075; G06T 7/602; G06T 2207/10012; G06T 2207/30181; G01N 9/00
USPC ............ 382/159, 100; 299/11, 2, 13, 17, 106, 299/19, 37.3, 16, 10; 37/304, 457, 348, 37/195, 446, 452, 455, 456; 701/50; 102/302; 405/130, 138; 340/435; 175/67; 414/694
See application file for complete search history.

(56) References Cited

U.S. PATENT DOCUMENTS

| | | | |
|---|---|---|---|
| 6,085,583 A | 7/2000 | Cannon et al. | |
| 6,928,384 B2 * | 8/2005 | Kochi | 702/155 |
| 7,215,811 B2 * | 5/2007 | Moselhi et al. | 382/156 |
| 7,313,506 B2 * | 12/2007 | Kacyra et al. | 703/6 |

(Continued)

FOREIGN PATENT DOCUMENTS

WO 2013043087 A1 3/2013

OTHER PUBLICATIONS

PCT International Search Report mailed Jul. 22, 2015 corresponding to PCT International Application No. PCT/US2015/023262 filed Mar. 30, 2015 (6 pages).

*Primary Examiner* — Sheela C Chawan (57) ABSTRACT

Provided is a method in which an excavation surface is scanned, the excavation surface shape is determined based on scanned excavation surface, an excavating path is identified from a mining excavation equipment, a volume of a material excavated by the mining excavation equipment is actively calculated based at least on the excavation surface shape and the excavating path of the mining excavating equipment, and a weight of the material excavated by the mining excavating equipment is actively calculated based on at least one density factor.

21 Claims, 8 Drawing Sheets

(56) References Cited

U.S. PATENT DOCUMENTS

| | | | |
|---|---|---|---|
| 7,832,126 B2* | 11/2010 | Koellner et al. | 37/348 |
| 8,320,627 B2* | 11/2012 | McDaniel et al. | 382/104 |
| 8,373,078 B2 | 2/2013 | Furem | |
| 8,694,258 B2* | 4/2014 | Haddad | 702/7 |
| 8,755,977 B2* | 6/2014 | Furem et al. | 701/50 |
| 8,930,091 B2* | 1/2015 | Upcroft et al. | 701/50 |
| 2004/0158355 A1 | 8/2004 | Holmqvist et al. | |
| 2005/0034902 A1 | 2/2005 | Furem | |
| 2008/0005938 A1 | 1/2008 | Aebischer et al. | |
| 2008/0282583 A1 | 11/2008 | Koellner et al. | |
| 2012/0304763 A1* | 12/2012 | Troxler | 73/32 R |
| 2014/0081506 A1 | 3/2014 | Pack et al. | |

* cited by examiner

METHODS AND SYSTEMS FOR ACTIVE LOAD WEIGHT FOR MINING EXCAVATING EQUIPMENT

BACKGROUND

1. Field

Aspects of the present invention relate to heavy equipment for surface mine field loading operations such as human-operated and/or autonomous mining shovels, draglines, and the like, and more particularly to systems used on such equipment to actively measure the net weight of excavated material in each load.

2. Description of Related Art

In large scale surface mining operations, excavating equipment of immense proportions is used to excavate and load material. Excavation is usually performed by mining shovels with a bucket capacity of dozens of tons per scoop.

Measurement systems have been developed to determine the net weight of material in the mining shovel bucket as it is transferred to the truck. However, upon determining that the net weight of the load exceeds required weight, the excavation equipment may be forced to dump the excavated material, causing the increase of an excavation cycle time, creating a safety hazard and, thus, higher overall labor and maintenance costs.

SUMMARY

Aspects of the present invention relate to methods and systems for active determination of a load weight for mining excavation equipment. In one embodiment, an excavation surface can be scanned, an excavation surface shape can be determined based on scanned excavation surface, an excavating path can be determined from a mining excavation equipment, a volume of the material excavated by the mining excavating equipment can be calculated based at least on the excavation surface shape and the excavating path of the mining excavating equipment, and a weight of the material excavated by the mining excavating equipment can be calculated based on at least one density factor.

DETAILED DESCRIPTION

Aspects of the present invention relate to methods and systems for active determination of a load weight for mining excavation equipment.

Figure 1:
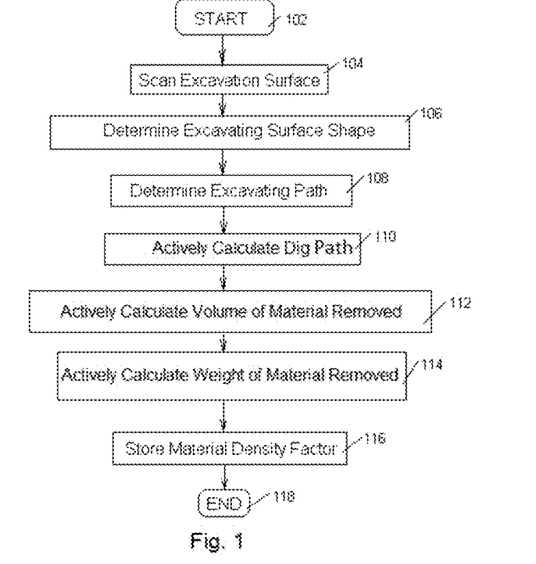
FIG. 1 illustrates a flow chart of a method for determining an active load weight for mining excavation equipment, in accordance with an exemplary embodiment.

FIG. 1 illustrates an exemplary method 100 for active determination of a weight of a material excavated by mining excavation equipment, according to an exemplary embodiment. The method 100 starts at step 102. At step 104, an excavation surface is scanned to determine shape of the excavation surface (i.e., bank). The excavation surface can be scanned with the use of a plurality of laser scanners adapted to provide a scan of a surrounding environment. The plurality of laser scanners can be locally mounted on the mining excavating equipment or remotely mounted. Remotely mounted laser scanners can be communicatively coupled to the equipment via wired and/or wireless transceivers.

Figure 2:
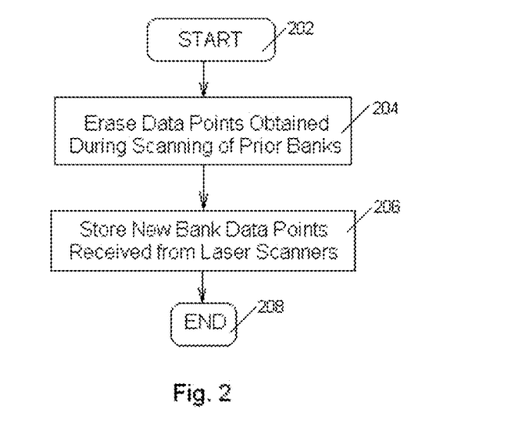
FIG. 2 illustrates a flow chart of method for obtaining a bank information, in accordance with an exemplary embodiment.

FIG. 2 illustrates an exemplary method 200 for receiving the bank information. The method 200 can be implemented to execute step 104 of FIG. 1. The method 200 starts at step 202 when new bank data (e.g., a plurality of laser scans of the bank) is received from the plurality of laser scanners. At step 204, all data points obtained during scanning of prior banks are erased from a data storage device for storing laser scans of previously scanned banks. In an embodiment, density factor values corresponding to a plurality of types of a material remain to be stored in a data storage device for storing density factor values. Density factor values are to be used to calculate an amount of material excavated in the future.

At step 206, the new bank data received from the plurality of laser scanners is stored in the data storage device for storing laser scans of the banks. The new bank information comprises a plurality of parameters defining the excavation surface, objects and/or topography that can interfere with activities of the shovel, and/or vehicles in the area of the shovel and/or haulage machines associated with the shovel. Method 200 concludes at step 208 and control is transferred back to method 100 of FIG. 1.

Figure 3:
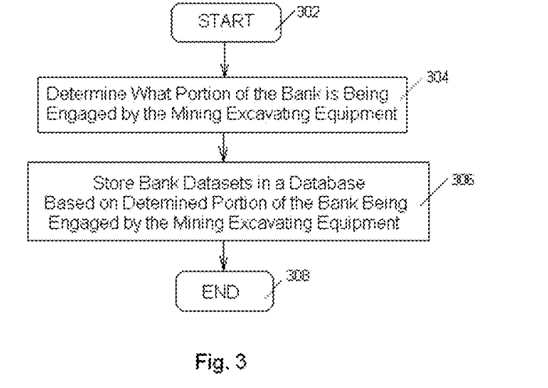
FIG. 3 illustrates a flow chart of a method for determining a dig face, in accordance with an exemplary embodiment.
Figure 11:
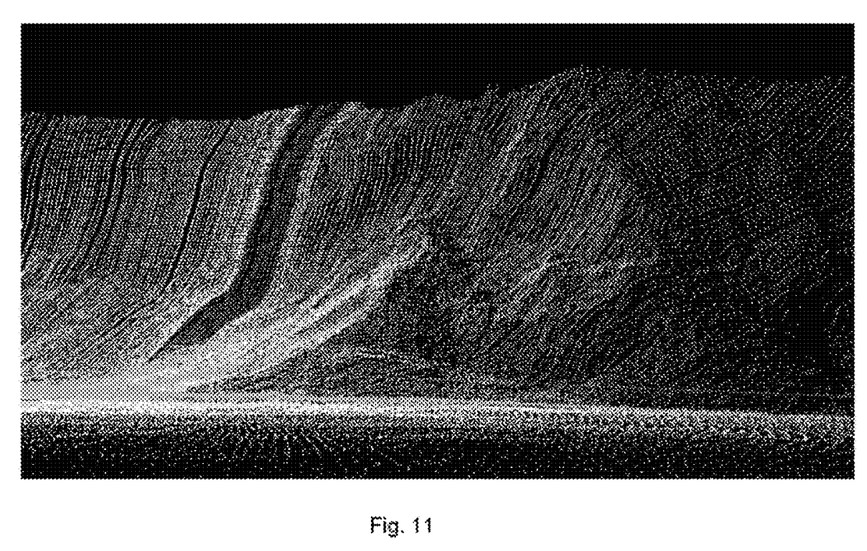
FIG. 11 illustrates a three-dimensional model of a bank.

Returning to FIG. 1, at step 106, a determination is made as to what portion of the bank data is being engaged by the mining excavating equipment (i.e., determine a dig face) and a bank shape is calculated. FIG. 3 illustrates an exemplary method 300 for determining a dig face. The method 300 can be used to implement a first portion of step 106 of method 100 illustrated in FIG. 1. The method 300 starts at step 302 when the mining excavating equipment enters the bank. At step 304, a determination is made as to what portion of the bank data is being engaged by the mining excavating equipment. As noted above, the shape of the bank can be determined with laser scanners that are mounted on the excavation equipment. As the machine rotates, these scanners take vertical distance readings. These scans are then added together to create a 3D model. FIG. 11 illustrates an exemplary 3D model generated based on the laser scans of the bank.

The shape of the bank is determined by analyzing X and Y (i.e., horizontal and vertical) coordinates of the scans taken near the front of the shovel. When the mining excavating equipment engages the bank, based on the angle of the mining excavating equipment a determination can be made as to which of the scans the mining excavating equipment is actually engaging. The location of the bucket of the mining excavating equipment is determined based on the position feedback received from the motion encoders. Using a geometric calculation, the encoder values can be converted into the same X/Y coordinate system used by the laser scanners such that the X and Y coordinates of the scans generated by the laser scanners can be compared with the X and Y coordinates calculated based on the encoder values. At step 306, a number of bank datasets is stored to be used for the volume and weight calculations. The method 300 is concluded at step 308 and control is relayed to a method for calculating a bank shape.

Figure 4:
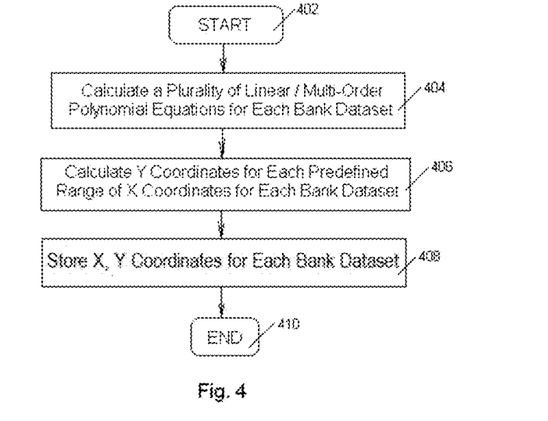
FIG. 4 illustrates a flow chart of a method for determining two-dimensional coordinates of a bank, in accordance with an exemplary embodiment.

FIG. 4 illustrates a method 400 for calculating a bank shape according to a first embodiment. The method 400 can be used to implement a second portion of step 106 of method 100 illustrated in FIG. 1. The method 400 starts at step 402 upon conclusion of the method 300 for determining a dig face. At step 404, a plurality of linear or multi-order polynomial equations is calculated. Specifically, using the data points received for the bank path, linear or polynomial equations are calculated to represent each of the curves of the bank path and digging path. In an embodiment, in order to increase calculation accuracy, the curves of each of the bank path and digging path are not represented by a single equation. Instead, each of the bank path and digging path are parsed into small sub segments of the curves and coefficients for each small portion of each curve are calculated. Calculating coefficients for each small portion of the curves will result in anomalies affecting only coefficients in small areas thereby improving the accuracy of the calculations.

At step 406, using the plurality of linear or multi-order polynomial equations established in step 404, the Y coordinates are calculated for a predefined range of X coordinates to generate Y coordinates for a known X range.

At step 408, the parameters of the bank shape (X and Y coordinates) are stored and at step 410 the method 400 returns control to the method 100 of FIG. 1.

Figure 5:
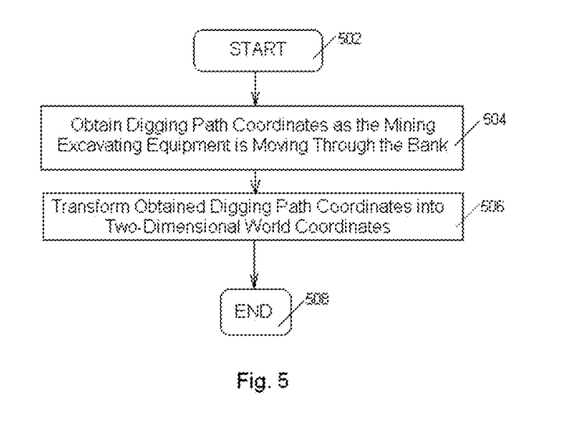
FIG. 5 illustrates a flow chart of a method for obtaining a digging path for an excavating equipment.

Returning to FIG. 1, at step 108, a path upon which the mining excavating equipment is traveling in the bank (i.e., digging path) is received. FIG. 5 illustrates an exemplary method 500 for receiving a digging path. The method 500 can be used to implement step 108 of FIG. 1. The method 500 starts at step 502 and at step 504, the digging path coordinates are obtained as the mining excavating equipment is moving through the bank. In an embodiment, the digging path coordinates are obtained using one or more motion encoders installed on the Shovel of the mining excavating equipment. At step 506, the obtained digging path coordinates are transformed into X and Y coordinates. At step 508 the method 500 concludes and control is transferred to the method 100 of FIG. 1.

Figure 6:
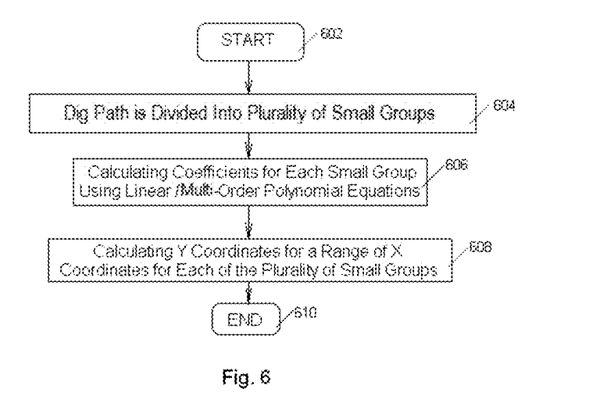
FIG. 6 illustrates a flow chart of a method for calculating pairs of coordinates for digging, in accordance with an exemplary embodiment.

At step 110 of FIG. 1, a dig path is calculated actively. In an embodiment, to actively calculate the dig path, the pairs of X and Y coordinates of the dig path have to be stored. FIG. 6 illustrates an exemplary method 600 for active calculation of the dig path. The method 600 can be used to implement step 110 of FIG. 1. The method 600 begins at step 602. At step 604, the dig path is divided into a plurality of small groups. At step 606, coefficients for each small group are calculated creating linear or multi-order polynomial equations in the manner similar to step 404 of method 400 described above. At step 608, using these linear or multi-order polynomial equations, the Y coordinates are calculated for the same preset range of X coordinates that was used in step 406 of method 400 described above. At step 610, the method 600 concludes and control is transferred to the method 100 of FIG. 1.

Figure 12:
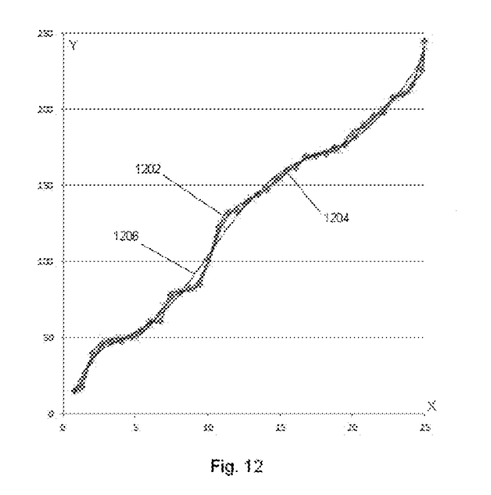
FIG. 12 illustrates a graphical representation of a bank as polynomials.

FIG. 12 illustrates an active generation of the bank shape. In particular FIG. 12 shows a recreated bank shape (1202), a recreated bank shape representing the bank as one polynomial (1206), and a recreated bank shape representing the bank as multiple polynomials (1204). As may be appreciated from the graph, using multiple polynomials to represent the bank shape is more accurate and results in more precise calculations.

Figure 7:
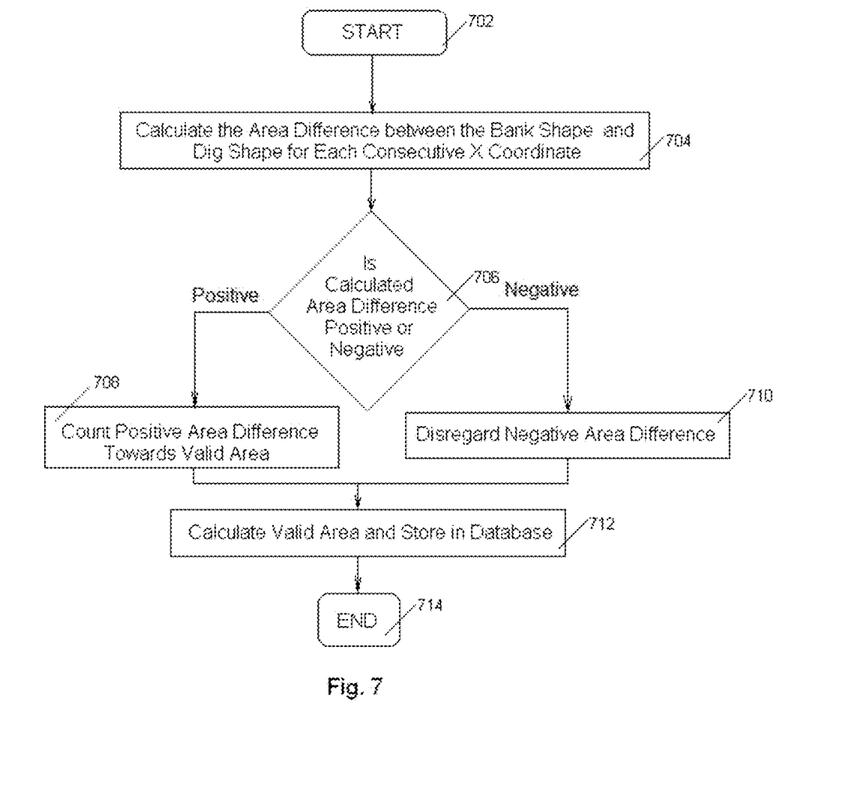
FIG. 7 illustrates a flow chart of a method for calculating an area removed by the excavating equipment.

With both the bank path and the digging path now having Y coordinates for all the same X values, it is possible to calculate what area was removed. For each consecutive X coordinate the area under the curve can be calculated for the bank path and the dig path. At step 112 of FIG. 1, a removed area is calculated. FIG. 7 illustrates an exemplary method 700 for calculating the removed area. The method 700 can be used to implement the method for calculating the removed area at step 112 of method 100 in FIG. 1. The method 700 starts at step 702.

In an embodiment, an equation to calculate an area under the curves can be presented as: Area=$0.5*\Delta X*[(Y_{bank1}+Y_{bank2})-(Y_{dig1}+Y_{dig2})]$, where $\Delta X$ is the change in x value between the two X coordinates; $Y_{bank1}$ is the height of the bank at the first coordinate; $Y_{bank2}$ is the height of the bank at the second coordinate; $Y_{dig1}$ is the height of the digging path at the first coordinate; and $Y_{dig2}$ is the height of the digging path at the second coordinate. It is to be understood that the equation presented above is an exemplary equation and that an area under the curves can be calculated using other equations.

At step 704, for each consecutive X coordinate the area under the curve can be calculated for the bank path and the dig path. If the area under the bank curve is larger than the area under the dig path, it can be concluded that the difference between the two is the material that was removed. If the area under the dig path is larger than the bank, the mining excavating equipment must have been moving above the bank. This calculation can be done for all X values, with the sum of all valid areas comprising the area of material that was removed.

At step 706, a determination is made as to whether calculated area difference is positive or negative. If the determination is made that the calculated area difference is positive, the method 700 proceeds to step 708 at which the positive area is counted towards the valid area. If the determination is made that the calculated area difference is negative, the method 700 proceeds to step 710 at which the negative area is disregarded because the calculated negative area is an indication that the mining excavating equipment was moving above the bank. At step 712, a value for the calculated valid area is calculated and stored. The method 700 concludes at step 714 and control is transferred back to the method 100 of FIG. 1.

Figure 8:
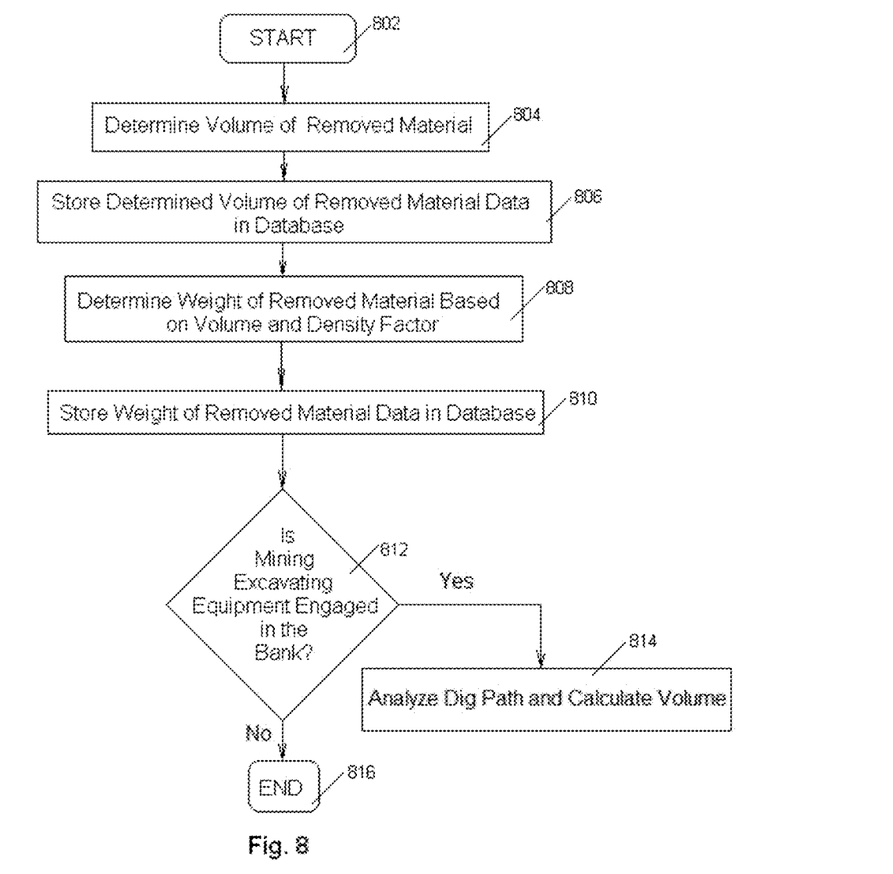
FIG. 8 illustrates a flow chart of a method for calculating weight of a material in a bucket.
Figure 13:
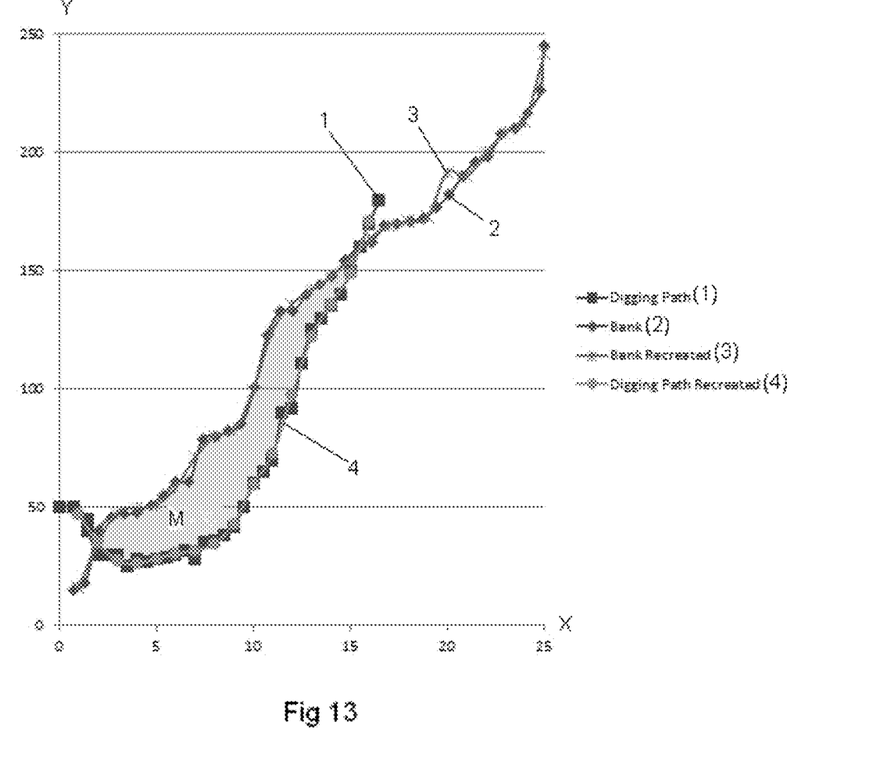
FIG. 13 illustrates a graphical representation of a material removed from the bank.

FIG. 13 illustrates calculating of the area digging path (line 1), a potential bank (line 2), and the area M between them that is considered material to have been removed:

Returning to FIG. 1, at step 114, a weight of the material in the bucket is calculated based on the area removed. FIG. 8 illustrates a method 800 for calculating weight of the material in the bucket according to an embodiment. The method 800 can be used to determine the weight of the material in the bucket. The method 800 starts at step 802. At step 804, the volume of material removed is determined by multiplying the calculated area removed by the known width of the bucket. It is to be understood that, in order to increase accuracy, the calculations in the previous steps could be performed for all engaged bank scans. At step 806, the determined volume of the material is stored in memory. At step 808, the weight of the material removed is determined by multiplying the stored volume of the material by a density factor value stored in a data storage device for storing density factor values. At step 810, the calculated weight of the material is stored. At step 812, a determination is made as to whether the mining excavation equipment is still engaged in the bank. If the determination is made that the mining excavation equipment is still engaged in the bank, the method 800 proceeds to step 814 at which steps of method 500 are repeated. If the determination is made that the mining excavation equipment is no longer engaged in the bank, the method 800 concludes at step 816 and control is returned to the method 100.

Figure 14:
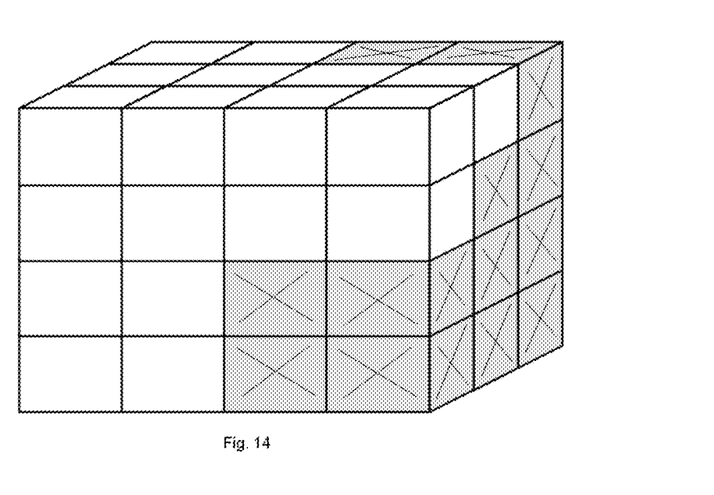
FIG. 14 illustrates an exemplary bank presented in a three-dimensional voxel.
Figure 15:
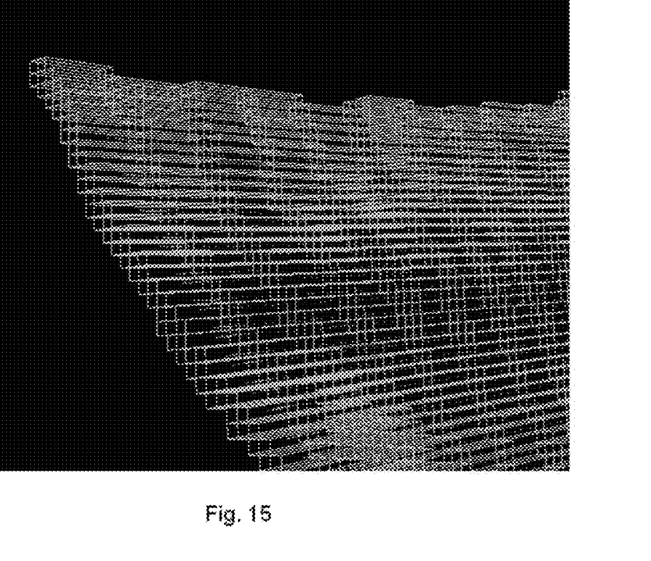
FIG. 15 illustrates a three-dimensional model of the bank using voxels.

A method for calculating the volume of the material in the bucket according to a second embodiment employs a 3D model of the bank represented in voxels. This method can be used in place of the volume calculation at step 804 of FIG. 8. FIG. 14 illustrates a voxel—a 3D-shaped box that is either turned "on" or "off." If any laser scanner, used to scan the bank illustrated on FIG. 15, detects an object within a certain voxel, this voxel is considered to be in the 'on' state (shaded and containing the "x" mark boxes). Voxel sizes are controlled by the user and will depend on the environment and the type of laser scanners.

Figure 16:
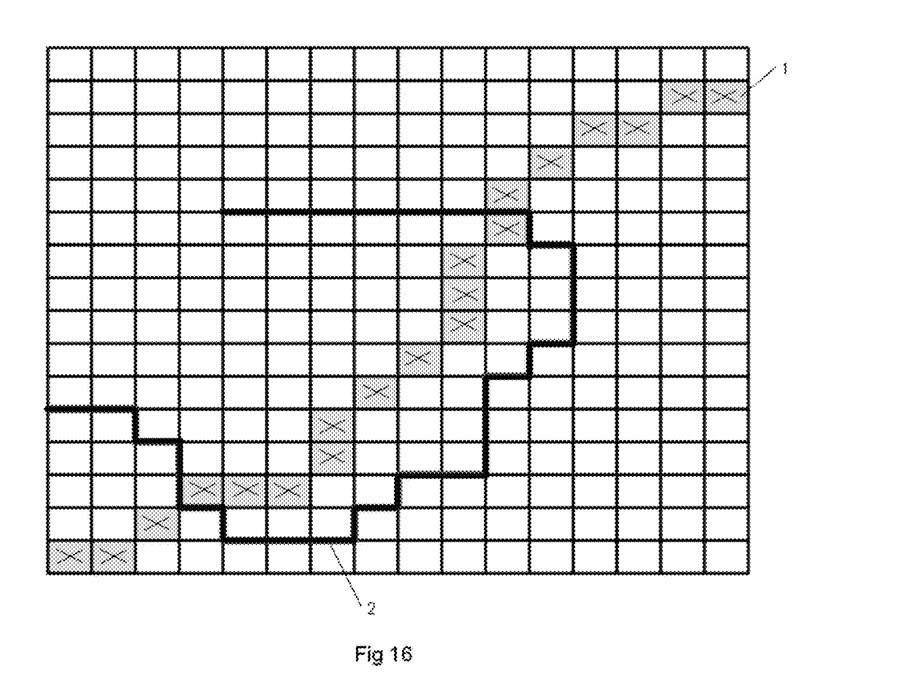
FIG. 16 illustrates a side-view of the bank presented in voxels, as well as a dig path.

With the bank being represented in voxels, the digging path and the bank shape can be compared. FIG. 16 illustrates a side view of a bank (voxels in the 'on state' represented in shaded boxes containing the "x" mark and designated as "1") and the digging path (shown by line "2"). It is to be understood that since the laser scanners cannot scan through material, the only part of the bank that is visible will be the front of the bank. It can be assumed that there are no holes in the bank and all voxels behind the scanned points should also be considered in the 'on state'.

A determination can be made that all voxels between the bank shape (shaded boxes 1 marked with the "x" sign) and the digging path (line 2) were removed. Since the volume of each voxel is known, the total volume removed can be calculated. It is to be understood that the described analysis is to be done for all voxels with which the mining excavating equipment engages.

Once the volume of the material is calculated using one of the two methods described above, the calculated volume is multiplied by a density factor. Such calculation will provide the weight of the bucket. As the density of material can depend on many factors, the density factor can be calculated by using a post-dig Load Weight calculating system. An example of the post-dig Load Weight calculation systems is described in detail in U.S. Pat. No. 8,373,078 "System and Method for Load Measuring by Motor Torque" issued Feb. 12, 2013, which is incorporated herein by reference in its entirety.

Figure 9:
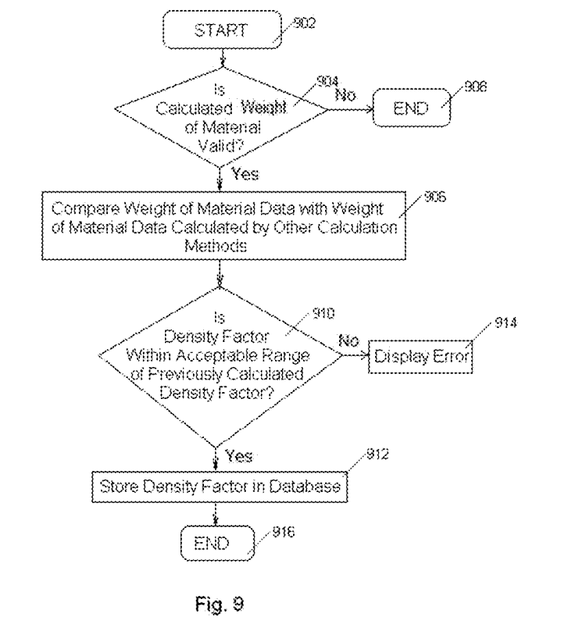
FIG. 9 illustrates a flow chart of a method for storing material density factor values.

Returning to FIG. 1, at step 116 of method 100, the density factor is stored. FIG. 9 illustrates an exemplary method 900 for storing the density factor. The method 900 starts at step 902. At step 904, a determination is made as to whether the weight of the material is within acceptable limit. Each time the mining excavation equipment concludes its operation, a value of the weight of the material calculated by multiplying the volume by a density factor is compared to a defined range. This range depends on physical abilities and size of the machine.

If the determination is made that the weight of the material is not within the acceptable limit, the method 900 is terminated at step 908 and control is returned to the method 100. If the determination is made that the weight of the material is within the acceptable limit, the method 900 proceeds to step 906 at which the volume of the material is compared to the weight value provided by other Load Weight calculation systems.

At step 910, a determination is made as to whether the value of the new density factor is within an acceptable range of the previously calculated density factor. If a difference between a currently calculated value of calculated density factor and previously calculated density factor is detected, the detected difference in density factor values is used to modify the density factor after each cycle. The updated density factor will then be used for the next iteration. If the determination is made that the value of the density factor differs by more than an acceptable limit, the method 900 proceeds to step 914 at which an error is generated and displayed.

It is to be understood that a change of the density factor value by more than an acceptable limit can occur because of incorrect calculations, incorrect (e.g., corrupt) data, or an actual change in density of the material. Upon generating and display of the error, the method 900 proceeds to step 916 at which the method 916 is concluded. If, at step 910, the determination is made that the value of the density factor does not differ from previous results by more than an acceptable limit, the method 900 proceeds to step 912 at which the recently calculated density factor is stored to be used for the next iteration. Then, the method 900 proceeds to step 916 at which the method 916 is concluded and control is returned to the method 100.

It is to be understood that a plurality of sensors, such as proprioceptive sensors, responsible for monitoring self-maintenance and controlling internal status can provide a wide variety of information regarding the mining excavation equipment, such as a measure angle at which the mining excavating equipment is positioned relative to the bank, a measured motor power and/or torque associated with the mining excavating equipment and the like to determine and/or optimize an excavating procedure. Information from the plurality of exteroceptive (e.g., proximity) sensors can be used to calculate and/or determine a two-dimensional and/or a three-dimensional model of the excavation surface. The two-dimensional and/or a three-dimensional model of the excavation surface can be prompted to operators of an excavating equipment or autonomous control system of the mining excavating equipment.

It is to be understood that information determined by the plurality of laser scanners can be wirelessly transmitted to the mining excavating equipment. In an embodiment, wirelessly transmitted information can be provided to an information device and/or a remote server. The wirelessly received information can be stored in a memory device and/or remotely reported via a client information device. The client information device can render and/or accumulate data across a plurality of excavating machines, haulage machines, hoists, shifts, time periods, operators, supervisors, and/or mines to allow for reporting and/or analysis.

In an embodiment, the mining excavating equipment can wirelessly receive information, such as weight information, from a remote wireless transmitter associated with, for example, the server and/or the client information device. Information received can, for example, be indicative of whether the material in the mining excavating equipment bucket should be loaded on the haulage machine. Information received can comprise an index of haulage machines assigned to the excavating equipment, performance related information related to material excavation, and/or repair recommendation related to the excavating equipment, etc.

Figure 10:
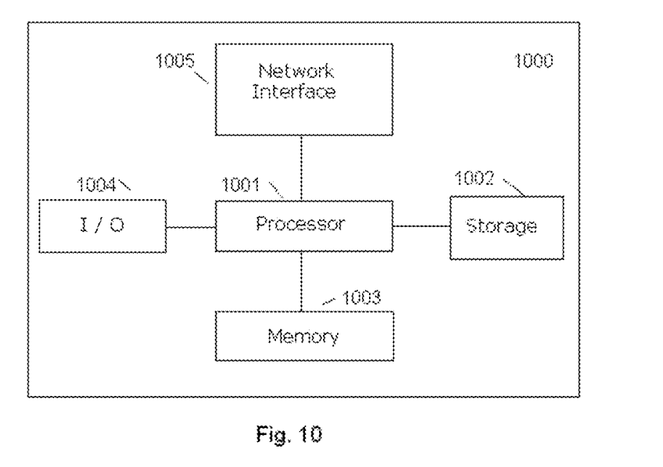
FIG. 10 illustrates an exemplary high-level block diagram of an exemplary computer that may be used for implementing active load weight measurement for excavating mining equipment.

FIG. 10 is a high-level block diagram of an exemplary computer that may be used for implementing preemptively determining a load weight for excavating mining equipment. Computer 1000 comprises a processor 1001 operatively coupled to a data storage device 1002 and a memory 1003. Processor 1001 controls the overall operation of computer 1000 by executing computer program instructions that define such operations. The computer program instructions may be stored in data storage device 1002, or other computer readable medium, and loaded into memory 1003 when execution of the computer program instructions is desired. Thus, the steps of exemplary methods of FIGS. 1-9 can be defined by the computer program instructions stored in memory 1003 and/or data storage device 1002 and controlled by processor 1001 executing the computer program instructions. For example, the computer program instructions can be implemented as computer executable code programmed by one skilled in the art to perform an algorithm defined by the method steps of FIGS. 1-9. Accordingly, by executing the computer program instructions, the processor 1001 executes an algorithm defined by the method steps of FIGS. 1-9. Computer 1000 also includes one or more network interfaces 1005 for communicating with other devices via a network. Computer 1000 also includes one or more input/output devices 1004 that enable user interaction with computer 1000 (e.g., display, keyboard, mouse, speakers, buttons, etc.).

Processor 1001 may include both general and special purpose microprocessors, and may be the sole processor or one of multiple processors of computer 1000. Processor 1001 may comprise one or more central processing units (CPUs), for example. Processor 1001, data storage device 1002, and/or memory 1003 may include, be supplemented by, or incorporated in, one or more application-specific integrated circuits (ASICs) and/or one or more field programmable gate arrays (FPGAs).

Data storage device 1002 and memory 1003 each comprise a tangible non-transitory computer readable storage medium. Data storage device 1002, and memory 1003, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1004 may include peripherals, such as a printer, scanner, display screen, etc. For example, input/output devices 1004 may include a display device such as a cathode ray tube (CRT), plasma or liquid crystal display (LCD) monitor for displaying information to the user, a keyboard, and a pointing device such as a mouse or a trackball by which the user can provide input to computer 1000.

In summary, aspects of the present invention relate to methods and systems for active determination of a load weight for mining excavation equipment. In one embodiment, an excavation surface can be scanned, an excavation surface shape can be determined based on scanned excavation surface, an excavating path can be determined from a mining excavation equipment, a volume of the material excavated by the mining excavating equipment can be calculated based at least on the excavation surface shape and the excavating path of the mining excavating equipment, and a weight of the material excavated by the mining excavating equipment can be calculated based on at least one density factor.

In an exemplary embodiment, the scanning of an excavation surface comprises scanning an excavation surface surrounding the mining excavating equipment using a plurality of laser scanners and generating a plurality of data points based on a plurality of images generated by the plurality of laser scanners.

In an exemplary embodiment, determining an excavation surface shape comprises combining the plurality of images into a three-dimensional model of the excavation surface, obtaining a plurality of sets of coordinates of each of the plurality of images, and determining the excavation surface shape based on the plurality of sets of coordinates.

In an exemplary embodiment, as the mining excavation equipment travels in the bank, the position of the bucket may be recorded using the encoders and an excavation path for the mining excavation equipment is determined, where determining an excavating path for the mining excavation equipment includes diving the plurality of data points into a plurality of groups and calculating polynomial coefficients for each of the plurality of groups, obtaining a plurality of sets of coordinates of each of the plurality of images in front of the mining excavating equipment, and determining the excavating path based on the plurality of sets of coordinates.

In an exemplary embodiment, wherein the calculating a volume of a material excavated by the mining excavation equipment includes calculating an area difference value between the excavation surface shape and the excavating path and including the area difference value in a total volume of the material excavated by the mining excavating equipment in response to determining that the area difference value is a positive value.

In an exemplary embodiment, if a value of an area removed in a single slice is known, calculating a weight of the material in a bucket of the mining excavating equipment includes determining a volume of the material in the bucket for each slice or by multiplying a value of an area removed by the bucket in a single slice by a value of a width of the bucket of the mining excavating equipment, determining the weight of the material in the bucket by multiplying the volume of the material in the bucket by the density factor, calculating a weight of the material using one of the weight calculation methods known in the art (e.g., post-dig method), determining a first density factor by dividing the weight of the material determined by one of the weight calculation methods known in the art method by the volume of the material, verifying that the weight of the material determined by one of the weight calculation methods described in the present disclosure is within a predetermined limit by comparing the weight of the material determined by one of the weight calculation methods known in the art with the weight of the material determined by a second weight calculating method using a second density factor, in response to verifying that the weight of the material determined by one of the weight calculation methods described in the present disclosure is within a predetermined limit, storing the first density factor in a database.

In an embodiment, wherein the calculating a volume of a material excavated by the mining excavation equipment includes using a 3D model of the bank represented in voxels so that a digging path and a bank shape can be compared and a determination can be made that all voxels between the bank shape and the digging path were removed. As the volume of each voxel is known, the total volume removed can be calculated.

One skilled in the art will recognize that an implementation of an actual computer or computer system may have other structures and may contain other components as well, and that FIG. 10 is a high level representation of some of the components of such a computer for illustrative purposes.

The invention claimed is:

1. A method for actively determining a load weight for mining excavation equipment, the method comprising:
   scanning an excavation surface;
   determining an excavation surface shape based on the scanned excavation surface;
   identifying an excavating path of a mining excavation equipment;
   calculating a volume of a material in a bucket of the mining excavation equipment based at least on the excavation surface shape and the excavating path of the mining excavating equipment; and
   calculating a weight of the material in the bucket of the mining excavating equipment based on the volume of the material in the bucket using at least one density factor,
   wherein the scanning an excavation surface comprises:
      scanning an excavation surface surrounding the mining excavating equipment using a plurality of laser scanners; and
      generating a plurality of data points based on a plurality of images generated by the plurality of laser scanners; and
   wherein the determining an excavation surface shape comprises:
      combining the plurality of images into a three-dimensional model of the excavation surface;
      obtaining a plurality of sets of coordinates for each of the plurality of images; and
      determining the excavation surface shape based on the plurality of sets of coordinates.

2. The method of claim 1, wherein the identifying an excavating path of the mining excavation equipment comprises:
   dividing the plurality of data points into a plurality of groups and calculating polynomial coefficients for each of the plurality of groups;
   obtaining a plurality of sets of coordinates of each of the plurality of images in front of the mining excavating equipment; and
   determining the excavating path based on the plurality of sets of coordinates.

3. The method of claim 1, wherein the calculating a volume of a material in a bucket of the mining excavation equipment based at least on the excavation surface shape and the excavating path of the mining excavating equipment comprises calculating an area of a material in the bucket of the mining excavation equipment by:
   calculating an area difference value between the excavation surface shape and the excavating path; and
   in response to determining that the area difference value is a positive value, including the area difference value in a total area of the material excavated by the mining excavating equipment.

4. The method of claim 1, wherein the calculating a weight of the material in a bucket of the mining excavating equipment comprises:
   determining a volume of the material in the bucket of the mining excavating equipment.

5. The method of claim 4, wherein the determining a volume of the material in the bucket comprises:
   multiplying a value of a width of the bucket of the mining excavating equipment by the total area of the material excavated by the mining excavating equipment; and
   determining the weight of the material in the bucket by multiplying the volume of the material in the bucket by the density factor.

6. The method of claim 4, wherein the determining a volume of the material in the bucket comprises:
   generating a three-dimensional model of the bank, the three dimensional model represented in voxels;
   comparing the digging path and the bank shape;
   determining the material removed from the bank based on a number of voxels between a visual representation of the bank shape and a visual representation of the digging path; and
   determining the volume of the material in the bucket based on a volume of each voxel in the three-dimensional model of the bank.

7. The method of claim 4, wherein the calculating a weight of the material in a bucket of the mining excavating equipment further comprises:
   calculating a weight of the material using a first weight calculation method;
   determining a first density factor by dividing the weight of the material determined by the first weight calculating method by the volume of the material;
   verifying that the weight of the material determined by the first weight calculating method is within a predetermined limit by comparing the weight of the material determined by the first weight calculating method with the weight of the material determined by a second weight calculating method using a second density factor;
   in response to verifying that the weight of the material determined by the first weight calculating method is within a predetermined limit, storing the first density factor in a database.

8. Apparatus for actively determining a load weight for mining excavation equipment, the method comprising:
   a processor; and
   a memory communicatively coupled with the processor and storing computer program instructions which, when executed on the processor cause the processor to perform operations comprising:
      scanning an excavation surface;
      determining an excavation surface shape based on the scanned excavation surface;
      identifying an excavating path of a mining excavation equipment;
      calculating a volume of a material in a bucket of the mining excavation equipment based at least on the excavation surface shape and the excavating path of the mining excavating equipment; and
      calculating a weight of the material in the bucket of the mining excavating equipment based on the volume of the material in the bucket using at least one density factor,
   wherein the scanning an excavation surface comprises:
      scanning an excavation surface surrounding the mining excavating equipment using a plurality of laser scanners; and
      generating a plurality of data points based on a plurality of images generated by the plurality of laser scanners; and wherein the determining an excavation surface shape comprises:
combining the plurality of images into a three-dimensional model of the excavation surface;
obtaining a plurality of sets of coordinates for each of the plurality of images; and
determining the excavation surface shape based on the plurality of sets of coordinates.

9. The apparatus of claim 8, wherein the identifying an excavating path of the mining excavation equipment comprises:
dividing the plurality of data points into a plurality of groups and calculating polynomial coefficients for each of the plurality of groups;
obtaining a plurality of sets of coordinates of each of the plurality of images in front of the mining excavating equipment; and
determining the excavating path based on the plurality of sets of coordinates.

10. The apparatus of claim 8, wherein the calculating a volume of a material in a bucket of the mining excavation equipment based at least on the excavation surface shape and the excavating path of the mining excavating equipment comprises calculating an area of a material in the bucket of the mining excavation equipment by:
calculating an area difference value between the excavation surface shape and the excavating path; and
in response to determining that the area difference value is a positive value, including the area difference value in a total area of the material excavated by the mining excavating equipment.

11. The apparatus of claim 8, wherein the calculating a weight of the material in a bucket of the mining excavating equipment comprises:
determining a volume of the material in the bucket of the mining excavating equipment.

12. The apparatus of claim 11, wherein the determining a volume of the material in the bucket comprises:
multiplying a value of a width of the bucket of the mining excavating equipment by the total area of the material excavated by the mining excavating equipment; and
determining the weight of the material in the bucket by multiplying the volume of the material in the bucket by the density factor.

13. The apparatus of claim 11, wherein the determining a volume of the material in the bucket comprises:
generating a three-dimensional model of the bank, the three-dimensional model represented in voxels;
comparing the digging path and the bank shape;
determining the material removed from the bank based on a number of voxels between a visual representation of the bank shape and a visual representation of the digging path; and
determining the volume of the material in the bucket based on a volume of each voxel in the three-dimensional model of the bank.

14. The apparatus of claim 11, wherein the calculating a weight of the material in a bucket of the mining excavating equipment further comprises:
calculating a weight of the material using a first weight calculation method;
determining a first density factor by dividing the weight of the material determined by the first weight calculating method by the volume of the material;
verifying that the weight of the material determined by the first weight calculating method is within a predetermined limit by comparing the weight of the material determined by the first weight calculating method with the weight of the material determined by a second weight calculating method using a second density factor;
in response to verifying that the weight of the material determined by the first weight calculating method is within a predetermined limit, storing the first density factor in a database.

15. A computer readable medium storing computer program instructions, which, when executed on a processor, cause the processor to perform operations comprising:
scanning an excavation surface;
determining an excavation surface shape based on the scanned excavation surface;
identifying an excavating path of a mining excavation equipment;
calculating a volume of a material in a bucket of the mining excavation equipment based at least on the excavation surface shape and the excavating path of the mining excavating equipment; and
calculating a weight of the material in the bucket of the mining excavating equipment based on the volume of the material in the bucket using at least one density factor,
wherein the calculating a weight of the material in a bucket of the mining excavating equipment comprises:
determining a volume of the material in the bucket of the mining excavating equipment comprising:
generating a three-dimensional model of the bank, the three-dimensional model represented in voxels;
comparing the digging path and the bank shape;
determining the material removed from the bank based on a number of voxels between a visual representation of the bank shape and a visual representation of the digging path; and
determining the volume of the material in the bucket based on a volume of each voxel in the three-dimensional model of the bank.

16. The computer readable medium of claim 15, wherein the scanning an excavation surface comprises:
scanning an excavation surface surrounding the mining excavating equipment using a plurality of laser scanners; and
generating a plurality of data points based on a plurality of images generated by the plurality of laser scanners.

17. The computer readable medium of claim 16, wherein the determining an excavation surface shape comprises:
combining the plurality of images into a three-dimensional model of the excavation surface;
obtaining a plurality of sets of coordinates for each of the plurality of images; and
determining the excavation surface shape based on the plurality of sets of coordinates.

18. The computer readable medium of claim 16, wherein the identifying an excavating path of the mining excavation equipment comprises:
dividing the plurality of data points into a plurality of groups and calculating polynomial coefficients for each of the plurality of groups;
obtaining a plurality of sets of coordinates of each of the plurality of images in front of the mining excavating equipment; and
determining the excavating path based on the plurality of sets of coordinates.

19. The computer readable medium of claim 15, wherein the calculating a volume of a material in a bucket of the mining excavation equipment based at least on the excavation surface shape and the excavating path of the mining excavating equipment comprises calculating an area of a material in the bucket of the mining excavation equipment by:

calculating an area difference value between the excavation surface shape and the excavating path; and in response to determining that the area difference value is a positive value, including the area difference value in a total area of the material excavated by the mining excavating equipment.

20. The computer readable medium of claim 15, wherein the determining a volume of the material in the bucket comprises:

multiplying a value of a width of the bucket of the mining excavating equipment by the total area of the material excavated by the mining excavating equipment; and determining the weight of the material in the bucket by multiplying the volume of the material in the bucket by the density factor.

21. The computer readable medium of claim 15, wherein the calculating a weight of the material in a bucket of the mining excavating equipment further comprises:

calculating a weight of the material using a first weight calculation method;

determining a first density factor by dividing the weight of the material determined by the first weight calculating method by the volume of the material;

verifying that the weight of the material determined by the first weight calculating method is within a predetermined limit by comparing the weight of the material determined by the first weight calculating method with the weight of the material determined by a second weight calculating method using a second density factor;

in response to verifying that the weight of the material determined by the first weight calculating method is within a predetermined limit, storing the first density factor in a database.

* * * * *